United States Patent
Van Acht et al.

(10) Patent No.: US 10,821,047 B2
(45) Date of Patent: Nov. 3, 2020

(54) METHOD FOR AUTOMATIC ALIGNMENT OF A POSITION AND ORIENTATION INDICATOR AND DEVICE FOR MONITORING THE MOVEMENTS OF A BODY PART

(75) Inventors: Victor Martinus Gerardus Van Acht, Waalre (NL); Nicolaas Lambert, Waalre (NL)

(73) Assignee: Koninklijke Philips N.V., Eindhoven (NL)

( * ) Notice: Subject to any disclaimer, the term of this patent is extended or adjusted under 35 U.S.C. 154(b) by 556 days.

(21) Appl. No.: 13/142,447

(22) PCT Filed: Jan. 12, 2010

(86) PCT No.: PCT/IB2010/050111
§ 371 (c)(1),
(2), (4) Date: Sep. 7, 2011

(87) PCT Pub. No.: WO2010/082156
PCT Pub. Date: Jul. 22, 2010

(65) Prior Publication Data
US 2011/0313327 A1    Dec. 22, 2011

(30) Foreign Application Priority Data
Jan. 16, 2009   (EP) .................................... 09150742

(51) Int. Cl.
| | |
|---|---|
| *A61B 5/11* | (2006.01) |
| *A61H 1/02* | (2006.01) |
| *A61B 5/00* | (2006.01) |
| *G06F 19/00* | (2018.01) |
| *G16H 40/40* | (2018.01) |

(52) U.S. Cl.
CPC ................. *A61H 1/02* (2013.01); *A61B 5/11* (2013.01); *A61B 5/4528* (2013.01);
(Continued)

(58) Field of Classification Search
CPC ....... A61B 5/11; A61B 5/4528; A61B 5/6824; A61B 5/6828; A61B 5/1121–1126;
(Continued)

(56) References Cited

U.S. PATENT DOCUMENTS

| | | | |
|---|---|---|---|
| 4,631,676 A | | 12/1986 | Pugh |
| 5,533,531 A | * | 7/1996 | Edwards et al. .............. 600/595 |

(Continued)

FOREIGN PATENT DOCUMENTS

| | | |
|---|---|---|
| CA | 2255094 A1 | 6/2000 |
| WO | 200218019 A1 | 3/2002 |
| WO | 2003014684 A1 | 2/2003 |

OTHER PUBLICATIONS

Fitzgerald, D. et al "Development of a wearable motion capture suit and virtual reality biofeedback system for the instruction and analysis of sports rehabilitation exercies" IEEE. EMBS 2007, Abstract Only.

*Primary Examiner* — Devin B Henson
*Assistant Examiner* — Huong Q. Nguyen

(57) ABSTRACT

A method for automatic alignment of a position and orientation indicator with respect to a body part is provided. The method includes the acts of attaching a position and orientation indicator to a body part; moving the body part and measuring movements of the position and orientation indicator; and exploiting physical constraints to motion to determine the alignment of the position and orientation indicator with respect to the body part.

15 Claims, 3 Drawing Sheets

(52) U.S. Cl.
CPC ........... *A61B 5/6824* (2013.01); *A61B 5/6828* (2013.01); *A61B 5/6831* (2013.01); *A61B 2505/09* (2013.01); *A61H 2201/165* (2013.01); *G06F 19/3481* (2013.01); *G16H 40/40* (2018.01)

(58) Field of Classification Search
CPC ..... A61B 5/1127; A61B 5/112; A61B 5/1114; A61B 5/1116; A61B 5/1118
USPC ........................................................ 600/595
See application file for complete search history.

(56) References Cited

U.S. PATENT DOCUMENTS

| | | |
|---|---|---|
| 6,487,906 B1 | 12/2002 | Hock |
| 6,514,219 B1* | 2/2003 | Guimond et al. ............ 600/595 |
| 6,997,882 B1 | 2/2006 | Parker et al. |
| 7,188,473 B1* | 3/2007 | Asada ..................... F03G 7/065 |
| | | 310/306 |
| 7,780,677 B2* | 8/2010 | Leitner ........................ 606/102 |
| 8,165,844 B2 | 4/2012 | Luinge et al. |
| 2003/0056385 A1 | 3/2003 | Leitner et al. |
| 2004/0106861 A1 | 6/2004 | Leitner |
| 2005/0143676 A1* | 6/2005 | De Guise ............... A61B 5/103 |
| | | 600/595 |
| 2007/0118056 A1* | 5/2007 | Wang .................... A61B 5/1116 |
| | | 600/595 |
| 2008/0262772 A1 | 10/2008 | Luinge |
| 2008/0281550 A1 | 11/2008 | Hogle |
| 2008/0285805 A1 | 11/2008 | Luinge et al. |
| 2009/0204031 A1* | 8/2009 | McNames ............ A61B 5/1071 |
| | | 600/595 |
| 2009/0259148 A1 | 10/2009 | Willmann et al. |

* cited by examiner

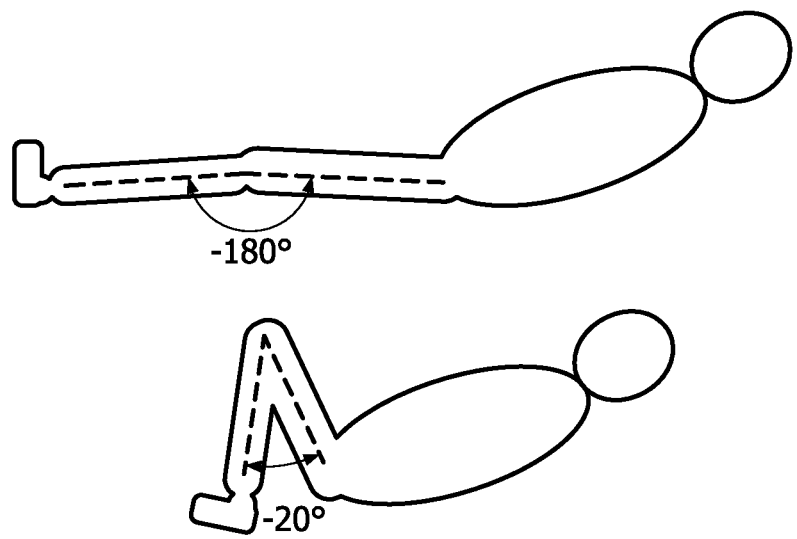
FIG. 6
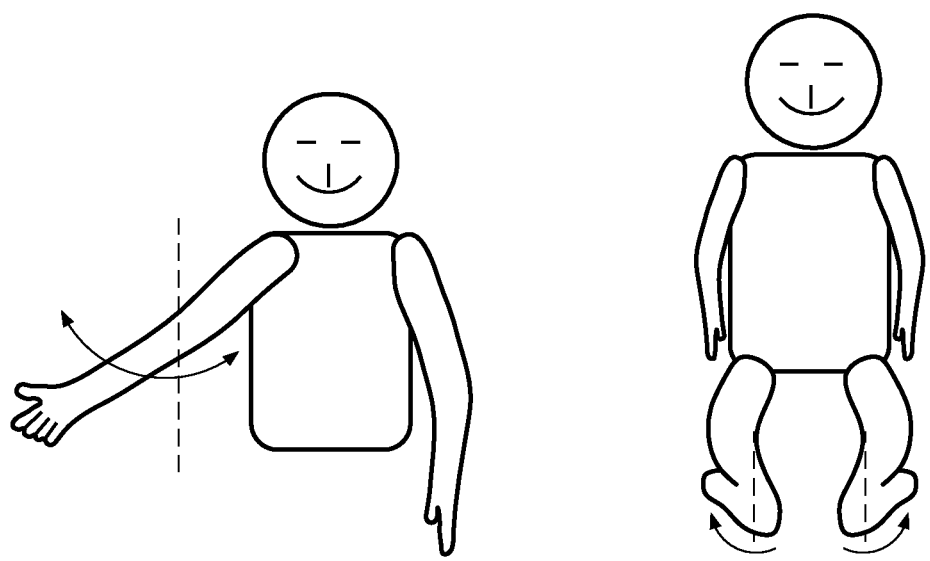
FIG. 7a
FIG. 7b

METHOD FOR AUTOMATIC ALIGNMENT OF A POSITION AND ORIENTATION INDICATOR AND DEVICE FOR MONITORING THE MOVEMENTS OF A BODY PART

FIELD OF INVENTION

The present invention relates to a method for automatic alignment of a position and orientation indicator with respect to a body part and to a device for monitoring the movements of a body part.

BACKGROUND OF THE INVENTION

Conventionally, physiotherapy is very labor intensive, since a physiotherapist can treat only one person at a time. As a result of this, conventional physiotherapy is rather expensive which results in that only a limited number of treatments is reimbursed to the patient in order to keep costs for the healthcare system low. The outcome for the patient would be improved if he/she could do more or longer physiotherapy exercises, but the costs for the physiotherapist which has to be present all the time prevents prescription of more and/or longer physiotherapy exercises.

In view of this, tools for therapists are being developed which enable the patients to execute physiotherapy exercises with less guidance from the therapist. Recently, it has been proposed to use position and orientation indicators for guiding physiotherapy patients on how to do their exercises in the correct way. According to this technique, the patient wears one or more position and orientation indicators for measuring the patient's movements. A computer evaluates the movements and can provide real-time feedback to the patient to motivate the patient to perform the exercises in the correct way. Further, the computer can generate progress reports for the therapist such that the therapist can guide for example 5 or 10 patients simultaneously working with such a type of system.

In order to properly evaluate which movements a patient performs during exercising, it is in many cases necessary to know the relative alignment of the position and orientation indicator (or position and orientation indicators) to the body part (or body parts) of the patient. For example, each position and orientation indicator can be provided with a local coordinate frame and this local coordinate frame can be misaligned to a local coordinate frame which is assigned to the body part to which the respective position and orientation indicator is attached. Such a misalignment is shown in FIG. 1 with respect to a position and orientation indicator having a local coordinate frame x_s and y_s which is attached to an upper arm u (as a body part) having a local coordinate frame x_u and y_u. In order to cope with such misalignments, it has been proposed to use a specific calibration procedure in which the patient is asked to take a predefined reference posture to aquire information about the alignment of the position and orientation indicator(s) with respect to the body part(s). This procedure is executed before the patient starts exercising. For example, according to a system known to the applicant, the position and orientation indicators are formed by motion sensors attached to different body parts and transmitting position and orientation information to a control unit. When the patient is in the reference posture (e.g. standing up right with the arms strictly down and the palms of the hands towards the legs) the motion sensor reading is stored as a reference reading. During normal operation of the system (i.e. when the patient performs the exercises), the current reading of the motion sensor can then be corrected using the reference reading (e.g. by "subtracting" the reference reading) in order to calculate the current orientation of the limbs from the orientation of the motion sensors.

However, such an explicit alignment procedure as described above is cumbersome and thus user-unfriendly. Further, if the patient does not accurately assume the reference posture during the calibration procedure (and this is not detected), all calculations based on the accuracy of the alignment calibration fail.

SUMMARY OF THE INVENTION

It is an object of the present invention to provide a method for alignment of a position and orientation indicator with respect to a body part and a device for monitoring the movements of a body part which enable reliable detection of body parts without requiring a separate calibration procedure.

This object is solved by a method for automatic alignment of a position and orientation indicator with respect to a body part. The method comprises the steps: attaching a position and orientation indicator to a body part; moving the body part and measuring movements of the position and orientation indicator; and exploiting physical constraints to motion to determine the alignment of the position and orientation indicator with respect to the body part. In this way, the alignment of the position and orientation indicator with respect to the body part is automatically determined without requiring a separate calibration procedure. The physical constraints to motion which are exploited can e.g. be physiological motion constraints such as the directivity of possible movements of a joint or another body part and/or physical motion constraints with respect to the motion of the position and orientation indicator which are caused by a specific way of attachment of the position and orientation indicator and/or further physical motion constraints. The term body part is used for parts of human or animal bodies. A body part may for instance be formed by an arm, a leg, a foot, a hand, or by portions thereof such as an upper arm, a lower arm, an upper leg, a lower leg, fingers, toes, etc. In particular, if an arm or a leg is considered as a body part in this application, a portion thereof will simultaneously be considered as a body part.

According to one aspect, the body part comprises at least one joint and physiological motion constraints of the at least one joint are exploited as physical constraints to motion. In this way, well-defined motion constraints which are directly linked to the body part to which the position and orientation indicator is attached are exploited for automatic position and orientation indicator alignment.

If the body part is an arm and the at least one joint is an elbow or the body part is a leg and the at least one joint is a knee, the method is particularly suited for position and orientation indicator alignment for monitoring typical physiotherapeutic exercises.

Preferably, the physical constraints to motion are exploited such that, when a motion of the body part is detected which is not possible in view of the physical constraints, it is judged that an alignment fault is present. In this case, misalignments can be quickly and reliably identified to achieve automatic alignment.

Preferably, the position and orientation indicator comprises a local coordinate system and is attached to the body part such that rotation about at least one axis of the local coordinate system with respect to the body part is prevented.

In this case, physical constraints to motion of the position and orientation indicator can be exploited due to the way of attachment. This allows more easily and reliably aligning the position and orientation indicator with respect to the body part without requiring a calibration procedure. If the position and orientation indicator is attached to the body part such that rotation about two axes of the local coordinate system with respect to the body part is prevented, alignment can be achieved even faster.

Preferably, at least a first position and orientation indicator and a second position and orientation indicator are attached to the body part and movements of one of the first and second position and orientation indicators with respect to the other one of the first and second position and orientation indicators are measured. In this way, e.g. the movements of at least one joint can be reliably exploited for automatic position and orientation indicator alignment. If the first position and orientation indicator is attached to the body part on one side of at least one joint and the second position and orientation indicator is attached to the body part on the opposite side of the at least one joint, automatic alignment is possible in a particularly efficient way.

The object is also solved by a device for monitoring the movements of at least one body part. The device comprises at least one position and orientation indicator adapted for being attached to a body part and a control unit adapted for measuring movements of the position and orientation indicator. The control unit is adapted to measure movements of the position and orientation indicator when the body part is moved and exploit physical constraints to motion to determine the alignment of the position and orientation indicator with respect to the body part from the measured movements. Thus, a device for monitoring the movements of at least one body part is provided which does not require a separate calibration procedure for alignment of the at least one position and orientation indicator.

Preferably, the device comprises at least a first position and orientation indicator and a second position and orientation indicator and the control unit is adapted to measure movements of one the first and second position and orientation indicators with respect to the other one of the first and second position and orientation indicators. In this case, for instance motions of at least one joint can reliably be exploited for automatic alignment of the position and orientation indicator. This is particularly the case if the first and second position and orientation indicators are adapted for attachment to the body part on opposite sides of at least one joint.

Preferably, the device is a physiotherapy monitoring device.

BRIEF DESCRIPTION OF THE DRAWINGS

Further features and advantages of the present invention will arise from the detailed description of embodiments with reference to the enclosed drawings.

FIG. 6 illustrates the motion range of a knee joint.

FIGS. 7a and 7b illustrate physiological motion constraints with respect to an elbow and with respect to human feet.

DETAILED DESCRIPTION OF EMBODIMENTS

First Embodiment

An embodiment of the present invention will now be described with reference to FIGS. 2 to 6. In the embodiment, the method for automatic alignment of a position and orientation indicator with respect to a body part will be exemplarily explained with respect to alignment of respective position and orientation indicators to an upper leg and a lower leg of a patient. Further, the device for monitoring the movements of at least one body part according to the embodiment is formed by a physiotherapy monitoring device. The device according to the embodiment is specifically adapted for monitoring movements of the leg of a patient, in particular for monitoring hip and knee exercises for physiotherapy patients. However, it should be noted that the invention is not limited to this type of application. For example, movements of other human or animal body parts can be monitored such as e.g. arms, elbows, shoulders, ankles, and the like. In particular, physiotherapeutic exercises can be monitored and/or guided. The device comprises a control unit 100 (see FIG. 2) which is connected (e.g. through wires or wireless) to the position and orientation indicators which will be described later on and is adapted such that the steps which will be described in following are performed by the device. In the embodiment described in the following, the position and orientation indicators are formed by motion sensors attached to respective body parts and transmitting position and orientation information to the control unit 100. However, it should be noted that the invention is not limited to this and can e.g. also be applied to other types of position and orientation indicators. For example, according to a system known to the applicant, the position and orientation indicators can also be formed by reference elements attached to different body parts, wherein position and orientation of the reference elements are detected by means of a suitable camera. One such system known to the applicant uses reflective balls attached to body parts, illuminating these reflective balls with infrared light, and detecting the position/orientation of the balls by detecting the reflected light with a suitable infrared camera.

Figure 2:
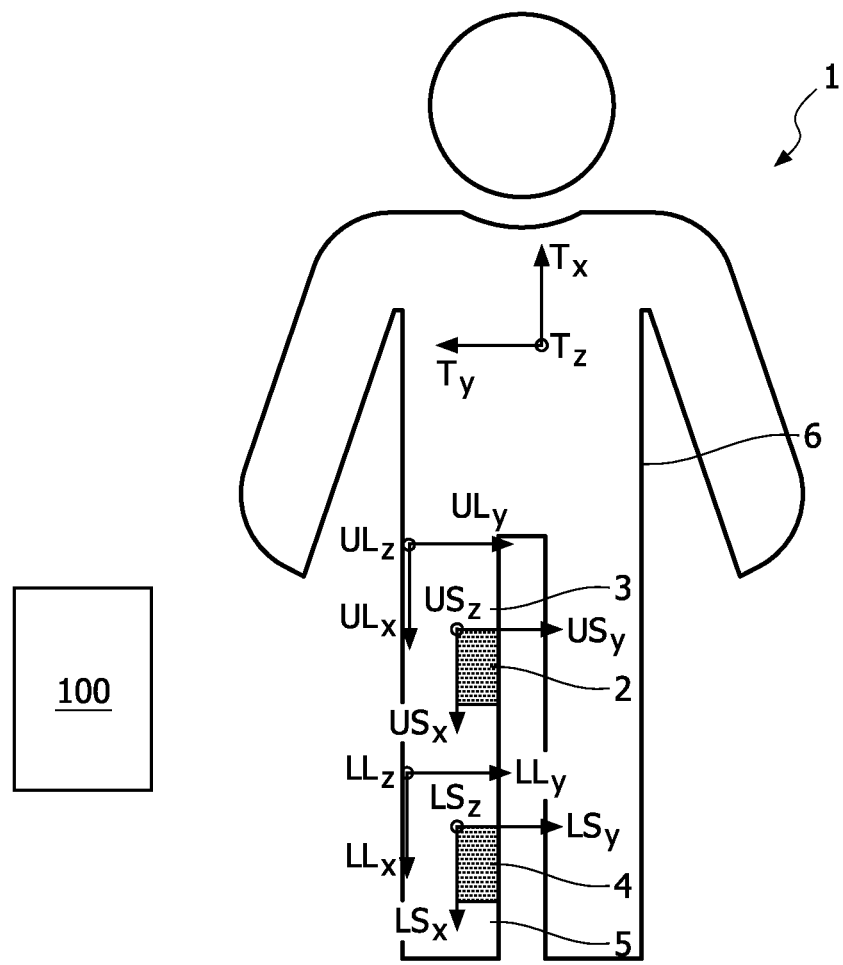
FIG. 2 schematically shows a human body comprising several body parts provided with position and orientation indicators and associated local coordinate systems.

FIG. 2 schematically shows a human body 1 comprising a plurality of body parts. In the example which will be described in the following, alignment of a first position and orientation indicator 2 with respect to an upper leg as a first body part 3 and alignment of a second position and orientation indicator 4 with respect to a lower leg as a second body part 5 will be explained. In the example which will be described, the steps for realizing this are implemented in the control unit 100 which is schematically depicted. A skilled person will understand that alignment of respective position and orientation indicators to other body parts can be performed in analogous or similar manner. The first position and orientation indicator 2 and the second position and orientation indicator 4 can e.g. be attached to the first body part 3 and the second body part 5 by means of elastic textile straps comprising small pouches in which the respective position and orientation indicators can be placed. In the example which will be described in the following, in order to measure the movements of the knee joint, one position and orientation indicator (first position and orientation indicator 2) is attached "above" the knee (i.e. attached to the upper leg) while another position and orientation indicator (second position and orientation indicator 4) is attached "below" the knee (i.e. attached to the lower leg).

In the example shown in FIG. 2, a (right-handed) local orthogonal coordinate frame is assigned to the first body part 3 (the upper leg). This local orthogonal coordinate frame comprises the axes $^{UL}x$, $^{UL}y$, and $^{UL}z$. $^{UL}z$ is chosen to point forward in the direction in which the face is directed (in a normal posture). $^{UL}x$ is chosen to point towards the foot, and $^{UL}y$ is chosen such that $^{UL}x$, $^{UL}y$, and $^{UL}z$ form a right-handed orthogonal coordinate frame. Similarly, a local orthogonal coordinate frame is assigned to the second body part 5 (the lower leg) comprising the axes $^{LL}x$, $^{LL}y$, and $^{LL}z$. $^{LL}z$ is chosen to point forward, $^{LL}x$ is chosen to point to the foot, and $^{LL}y$ is chosen such that a right-handed local orthogonal coordinate frame is formed.

Figure 3:
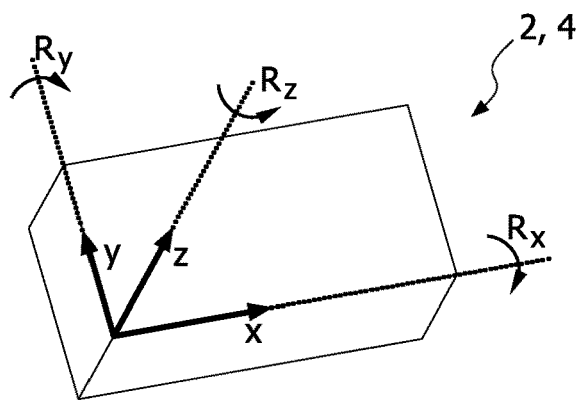
FIG. 3 schematically illustrates the orientation of a local position and orientation indicator coordinate system.

In a similar manner, local coordinate frames are assigned to the first position and orientation indicator 2 and to the second position and orientation indicator 4. The local coordinate frame assigned to the first position and orientation indicator 2 comprises the axes $^{US}x$, $^{US}y$, $^{US}z$. The local coordinate frame assigned to the second position and orientation indicator 4 comprises the axes $^{LS}x$, $^{LS}y$, and $^{LS}z$. The assignment of the local coordinate frames to the first and second position and orientation indicators 2 and 4 is schematically shown in FIG. 3 where x corresponds to $^{US}x$ or $^{LS}x$, y to $^{US}y$ or $^{LS}y$, and z corresponds to $^{US}z$ or $^{LS}z$, respectively. Rx is used to indicate a rotation about the axis x, Ry to indicate a rotation about y, and Rz to indicate a rotation about z.

In an optimum situation corresponding to perfect alignment of the first position and orientation indicator 2 to the first body part 3, the direction of $^{US}x$ corresponds to $^{UL}x$, the direction of $^{US}y$ corresponds to $^{UL}y$, and the direction of $^{US}z$ corresponds to $^{UL}z$. Similarly, for a perfect alignment of the second position and orientation indicator 4 to the second body part 5 the direction of $^{LS}x$ corresponds to $^{LL}x$, the direction of $^{LS}y$ corresponds to $^{LL}y$, and the direction of $^{LS}z$ corresponds to $^{LL}z$. Such a perfect alignment situation is schematically depicted in FIG. 2.

Further, in FIG. 2 a local coordinate frame is assigned to the torso 6 with the axis $^{T}z$ pointing forward, the axis $^{T}x$ pointing towards the head, and $^{T}y$ being chosen such that a right-handed orthogonal local coordinate frame is formed. It should be noted that local coordinate frames can be assigned to other body parts in a corresponding way. Further, position and orientation indicators could additionally or alternatively be attached to other body parts.

It has been described that, in a perfect alignment situation, the coordinate frames of the first position and orientation indicator 2 ($^{US}x$, $^{US}y$, $^{US}z$) and the first body part 3 ($^{UL}x$, $^{UL}y$, $^{UL}z$) would be equal and the coordinate frames of the second position and orientation indicator 4 ($^{LS}x$, $^{LS}y$, $^{LS}z$) and the second body part 5 ($^{LL}x$, $^{LL}y$, $^{LL}z$) would be equal.

Figure 1:
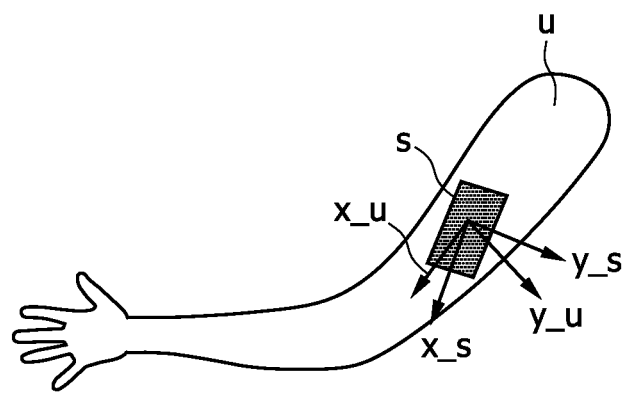
FIG. 1 schematically shows an example for misalignment between a position and orientation indicator and a body part.

However, in a real situation in which the position and orientation indicators are attached to respective body parts (e.g. by flexible textile straps), this perfect situation will normally not be present. A certain misalignment between the coordinate frames of the first position and orientation indicator 2 and the first body part 3 will be present, i.e. the directions of the corresponding axes will differ. Similarly, a certain misalignment between the coordinate frames of the second position and orientation indicator 4 and the second body part 5 will be present. Such a situation has been described above with respect to FIG. 1 (with respect to two axes in FIG. 1). If the alignment between the position and orientation indicators and the respective body parts was known, the readings of the position and orientation indicators could be corrected accordingly.

In the following, a method for automatically aligning a position and orientation indicator to the corresponding body part, i.e. aligning the local position and orientation indicator coordinate frame and the local body part coordinate frame, will be described. Exemplarily, alignment of a first position and orientation indicator 2 to the upper leg (as a first body part) and alignment of a second position and orientation indicator 4 to the lower leg (as a second body part) will be described. In the example given, the alignment will be performed based on movements of the knee joint situated between the first and second position and orientation indicators 2, 4.

For achieving alignment of the position and orientation indicator to the corresponding body part, physical motion constraints are exploited. Context information on where the respective position and orientation indicator is located on a body part is used. In particular, the information is exploited whether a particular joint is capable of rotating in all degrees of freedom (such as in case of a hip joint or shoulder joint) or not (such as in case of the knee or elbow joint). Further, the possible range of motion of a particular joint is exploited. In other words, if the position and orientation indicator measures a movement which is (physically) not possible, this must be due to a position and orientation indicator to body part alignment fault. The alignment between the position and orientation indicator and the body part is then updated in such a way that the movement is not "impossible" any longer. This will be exemplarily explained based on movements of a knee joint in the following.

It has been described above that the first and second position and orientation indicators 2, 4 can e.g. be attached to the first body part 3 and the second body part 5, respectively, by means of flexible elastic straps comprising pouches for accommodating the respective position and orientation indicators. In this case, at least one rotational degree of freedom of the alignment between the position and orientation indicator and the corresponding body part can be made fixed due to specific attachment. This will be described in more detail with reference to FIGS. 4a to 4c for the attachment of the first position and orientation indicator 2 to the upper leg and of the second position and orientation indicator 4 to the lower leg. In the example shown in FIGS. 4a to 4c, the first position and orientation indicator 2 is attached to the first body part 3 by means of a strap 7 and the second position and orientation indicator 4 is attached to the second body part 5 by means of a strap 9. The shape of the straps 7, 9 and of the first and second position and orientation indicators 2, 4 is selected such that rotation about the local z-axis (e.g. the $^{US}z$-axis or the $^{LS}z$-axis) of the position and orientation indicators 2, 4 is prevented.

Figures 4A, 4B, 4C:
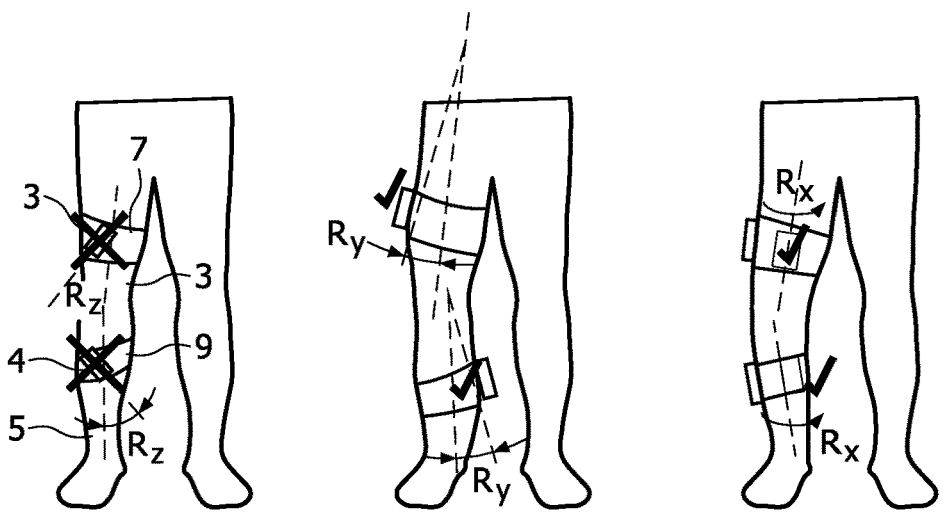
FIGS. 4a to 4c schematically illustrates different degrees of freedom in orientation between local position and orientation indicator coordinate systems and body parts.

FIG. 4a schematically shows that, in case of a suitable design of the straps and of the position and orientation indicators, rotation about the local z-axis of the respective position and orientation indicators is prevented. However, FIGS. 4b and 4c schematically show that the orientation of the position and orientation indicators 2, 4 with respect to their local y-axis (FIG. 4b) and with respect to their local x-axis (FIG. 4c) is not fixed. In other words, since the way of attachment restricts a rotation of the position and orientation indicator about its local z-axis, this alignment parameter can be assumed to be zero or some other constant. With respect to the local x-axis of the respective position and orientation indicator, in case of the body part being a (lower or upper) leg, rotation about the x-axis is not restricted (i.e. whether the position and orientation indicator is worn on the "front" of the leg or on the "side" of the leg). Similarly, with respect to the local y-axis of the position and orientation indicator, the local y-axis is not fixed, since it cannot be predetermined how cone shaped the patient's leg is. As a consequence of this possible misalignment of the respective position and orientation indicator with respect to the corresponding body part, two alignment parameters (the position of the x-axis and the position of the y-axis of the local position and orientation indicator coordinate system with respect to the local coordinate system of the corresponding body part) have to be estimated and/or tracked.

Now, it will be explained how further physical motion constraints are used for aligning the local coordinate systems of the respective position and orientation indicators to the local coordinate systems of the respective body parts. With respect to the embodiment this will done with respect to a motion of the knee joint.

If the patient wearing the first position and orientation indicator 2 attached to the upper leg as a first body part 3 and the second position and orientation indicator 4 attached to the lower leg as a second body part 5 moves the knee joint, it is possible to calculate the rotation axis around which the second position and orientation indicator 4 (the lower leg position and orientation indicator) rotates with respect to the first position and orientation indicator 2 (the upper leg position and orientation indicator) from the readings of both position and orientation indicators. This rotation axis will be equal to the knee joint. The rotation axis can e.g. be expressed in the local coordinate system of the second position and orientation indicator 4. (It should be noted that the rotation axis can of course also be expressed in the local coordinate system of the first position and orientation indicator 2). Now, the knowledge that the rotation can only be caused by the knee joint and the knowledge about the physiological constraints of the knee joint can be used as physical constraints for aligning the local position and orientation indicator coordinate systems with the local body part coordinate systems. Since the knee joint has substantially only one degree of freedom (i.e. only rotation about the $^{UL}y/^{LL}y$ axis in FIG. 2 is possible), the alignment of the local coordinate frame of the second position and orientation indicator 4 can be found by finding the rotation of the second position and orientation indicator 4 such that the rotation of the knee expressed in the local coordinate frame of the second position and orientation indicator 4 is also along the corrected $^{LS}y$ axis (see FIG. 2). This means that the orientation of the local position and orientation indicator coordinate frame has to become mathematically aligned to the local body part coordinate frame.

Further, there is the additional physical constraint that the way of attachment (e.g. by the flexible textile strap) prevents the second position and orientation indicator from rotating around its local $^{LS}z$-axis as has been described above. This further physical constraint is also exploited for alignment. As a consequence of this further constraint, for finding the alignment rotation of the second position and orientation indicator, the second position and orientation indicator should be rotated only around its $^{LS}x$-axis and its $^{LS}y$-axis in order to align the knee joint rotation axis with the corrected $^{LS}y$-axis.

The local coordinate frame of the first position and orientation indicator 2 can be aligned to the local coordinate frame of the first body part 3 in a similar manner.

To summarize the principle which has been described above: In principle, the alignment between the second position and orientation indicator 4 and the second body part 3 has three degrees of freedom (3 unknowns). The same holds for the alignment between the first position and orientation indicator 2 and the first body part 3. Because of the physical constraint that the knee joint has (only one degree of freedom, thus 1 unknown) two equations with 3 unknowns would result. However, since there is the further physical constraint that the way of attachment restricts one degree of freedom of the alignment (namely a rotation around the $^{US}z$-axis or the $^{LS}z$-axis, respectively), two equations with two unknowns result. Such a situation is uniquely solvable for both the first position and orientation indicator 2 and the second position and orientation indicator 4.

In the following it will be described how the position and orientation indicator alignment described above with words is achieved from a mathematical point of view. Again, the mathematical description will be exemplarily given for the situation of the first and second position and orientation indicators 2, 4 attached to the upper leg and the lower leg on different sides of the knee joint, respectively.

In the following description, all orientations (of axes of the respective local coordinate systems) will be expressed as quaternions. However, the algorithms could also be expressed using another representation of 3-dimensional orientations such as Euler angles or rotation matrices, albeit with a little more work.

First, it will be described how the rotation axis of the knee joint can be found in the present example.

The orientation of the first position and orientation indicator 2 expressed in a world-fixed reference coordinate frame (a global coordinate frame) is given by the quaternion $^{W}Q_{US}$ and the orientation of the second position and orientation indicator 4 expressed in the world-fixed reference coordinate frame is given by $^{W}Q_{LS}$, wherein a quaternion $^{A}Q_{B}$ expresses a rotation (or coordinate transformation) from frame B to frame A.

Then, the difference in orientation between the first position and orientation indicator 2 and the second position and orientation indicator 4 ($^{LS}Q_{US}$) is given by:

$$^{LS}Q_{US} = {^{W}Q_{LS}}^{*} \otimes^{W} Q_{US} \quad (1)$$

where $\otimes^{W}$ denotes the quaternion product and Q* denotes the quaternion conjugate.

When, during movement of the first and second position and orientation indicators relative to each other (which is a motion of the knee joint in the present example), the instantaneous values of $^{LS}Q_{US}$ are passed through a low pass filter with a cut-off frequency of for example 0.3 Hz, the average difference in orientation between the first position and orientation indicator 2 and the second position and orientation indicator 4 denoted by $\lfloor^{LS}Q_{US}\rfloor$ is obtained.

The difference between the instantaneous value of $^{LS}Q_{US}$ and its average value $\lfloor^{LS}Q_{US}\rfloor$ can be calculated. This difference will be called $^{LS}Q_{\lfloor LS \rfloor}$ and is given by the following equation:

$$^{LS}Q_{\lfloor LS \rfloor} = {^{LS}Q_{US}} \otimes \lfloor^{LS}Q_{US}\rfloor \quad (2)$$

The difference $^{LS}Q_{\lfloor LS \rfloor}$ can be interpreted as the instantaneous difference between, on one hand, the current difference in orientation between the first position and orientation indicator orientation and the second position and orientation indicator orientation and, on the other hand, the average difference in orientation between the first position and orientation indicator orientation and the second position and orientation indicator orientation. And obviously, the difference between the instantaneous value and the average value is caused by movement of the knee joint.

When the knee joint doesn't move at all, the instantaneous and the average value are equal and thus the difference $^{LS}Q_{[LS]}$ is equal to zero. When the knee joint does move, $^{LS}Q_{[LS]}$ takes values on both sides of a line through the origin, the line expressing exactly the rotation axis of the knee expressed in the coordinate frame that is fixed to the second position and orientation indicator 4.

Figure 5:
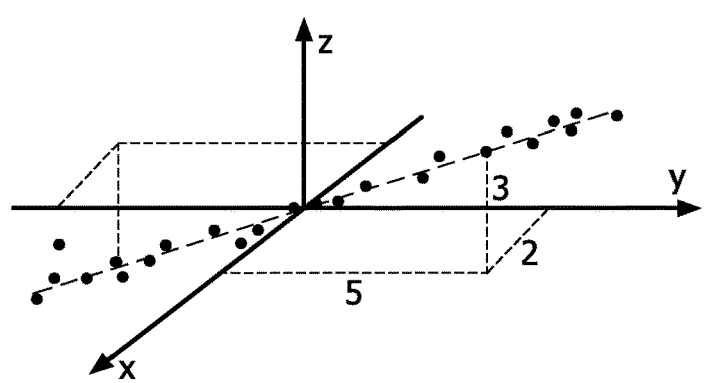
FIG. 5 shows an example of a plot used for determining the rotation axis of a joint.

In order to obtain the direction of this rotation axis, the w-component of the quaternion is omitted and the x, y and z component of different samples of the 4-dimensional quaternion $^{LS}Q_{[LS]}$ are plotted in a 3 dimensional graph. A plot like the dots in FIG. 5 is obtained. As can be seen in FIG. 5, the dots (samples of $^{LS}Q_{[LS]}$ with the w-component omitted) lie on a line (indicated by a dashed line in FIG. 5). In this representation, the x-, y- and z-components of $^{LS}Q_{[LS]}$ are along the axes.

Now, the final step is to perform a principal component analysis on the x, y and z components of data points of $^{LS}Q_{[LS]}$ to find the main rotation axis (that is, the dashed line in FIG. 5). It should be noted that a slightly modified version of the standard principle component analysis can be used since it is known that the rotation axis crosses the origin of the orientation space by definition. The result is the rotation axis of the knee. The rotation axis is expressed as a vector, expressed in the coordinate system that is fixed to the second position and orientation indicator 4. In the example of FIG. 5, the rotation axis would be (x, y, z)=(2, 5, 3).

It is also possible to express the rotation axis of the knee in the coordinate system of the first position and orientation indicator 2 (or a world-fixed reference frame for that matter).

It should be noted that this method does not only apply to find the rotation axis of the knee, obviously it can be used to find the rotation axis of any part of the body. For example, the same algorithm can be used to find the rotation axis of the hip to see in which direction an upper leg of a patient swings with respect to the patient's torso. Of course, it can also be used for other body parts (appropriately provided with position and orientation indicators).

Thus, a vector has been obtained (e.g. expressed in the local coordinate system of the second position and orientation indicator; however, it should be noted that the vector could also be expressed in another coordinate system such as that of the first position and orientation indicator or in a global coordinate system). In the following it will be described how the position and orientation indicator alignment of e.g. the second position and orientation indicator 4 can be calculated.

Thus, the alignment quaternion of the second position and orientation indicator 4 is to be calculated under the assumption that the second position and orientation indicator 4 cannot rotate around its local z-axis (see explanation above with respect to FIGS. 4a to 4c). This means that if a rotation $^{UL}Qalign_{US}$ is applied to the vector v representing the rotation axis (with length 1), a vector is obtained that is in the y-direction (with length 1), as the coordinate systems of the first body part 3 and the second body part 5 were chosen such that the rotation axis of the knee joint was in the y-direction. Hence, the following equation results:

$$\begin{bmatrix} 0 \\ 1 \\ 0 \end{bmatrix} = {}^{UL}Qalign_{US} \otimes v \otimes {}^{UL}Qalign^*_{US} \quad (3)$$

Since rotation of the position and orientation indicator around its local z-axis is prevented, the z-component of $^{UL}Qalign_{US}$ is equal to zero and the following is given:

$$^{UL}Qalign_{US} = \begin{bmatrix} \sqrt{1 - q_x^2 - q_y^2} \\ q_x \\ q_y \\ 0 \end{bmatrix} \quad (4)$$

Substituting equation (4) in equation (3) and solving for $q_x$ and $q_y$ in terms of the individual components of v, $v_x$, $v_y$, and $v_z$ yields the following equation.

$$^{UL}Qalign_{US} = \begin{cases} \begin{bmatrix} \dfrac{1}{v_z\sqrt{2+2v_y}} & \dfrac{v_y+1}{v_z^2\sqrt{2+2v_y}} & -\dfrac{v_x}{v_z^2\sqrt{2+2v_y}} & 0 \end{bmatrix} \text{ or} \\ \begin{bmatrix} \dfrac{1}{v_z\sqrt{2+2v_y}} & \dfrac{v_y-1}{v_z^2\sqrt{2+2v_y}} & -\dfrac{v_x}{v_z^2\sqrt{2+2v_y}} & 0 \end{bmatrix} \end{cases} \quad (5)$$

It should be noted that equation (5) shows that in the case of $v_z$ being equal to zero there is no solution to equation (3). This would be the situation where the position and orientation indicator and the corresponding body part are not perfectly aligned, but the only way to rotate the position and orientation indicator coordinate system to the limb coordinate system would be a single rotation around the z-axis of the position and orientation indicator coordinate system. This was assumed to be impossible because of the way of fixation (e.g. by a textile strap), so this situation will not occur. It should further be noted that equation (5) gives two solutions for $^{UL}Qalign_{US}$. These solutions differ by 180 degrees and result in that it cannot be determined whether the position and orientation indicator is mounted 'up side down' on the body part.

The automatic alignment method described thus far does not give any alignment around the $^{UL}y$ (or $^{LL}y$) axis, as this is the axis around which the knee is rotating. In order to obtain a proper position and orientation indicator alignment around the $^{UL}y$ (or $^{LL}y$) axis, the range of motion of the knee can be used: The knee cannot be stretched further than 180 degrees and also not bend more than e.g. 20 degrees, as indicated in FIG. 6.

So, if the position and orientation indicator outputs show that the knee joint is making a movement that is beyond this range, it is clear that the alignment of the position and orientation indicator around the $^{UL}y$ (or $^{LL}y$) axis is wrong and needs to be adapted. According to the embodiment, the alignment of both the first position and orientation indicator and the second position and orientation indicator is adapted in such a way that the maximum range of motion is no longer violated.

Modification of the First Embodiment

According to a preferred modification, the first and second position and orientation indicators 2, 4 are mounted on the first and second body parts 3, 5 such that the $^{US}z$ (or $^{LS}z$) axes of the position and orientation indicators are substantially in the same direction as the $^{UL}y$ (or $^{LL}y$) axes. This means that the position and orientation indicators are mounted on the 'side' of the legs in the example given (so not on the front as shown in FIG. 2). This mounting does not need to be very accurate.

With this arrangement, the full alignment between the position and orientation indicators 2, 4 and the body parts 3, 5 can be determined, because now the $^{US}z$ (or $^{LS}z$) axis of the respective position and orientation indicator (around which it was assumed that the position and orientation indicator could not rotate because of the way of fixation, e.g. by a textile strap) is roughly in the same direction as $^{UL}y$ (or $^{LL}y$) of the first or second body part (around which the automatic alignment method of the previous sections does not give information). So, although the motions of the knee do not give alignment information around the $^{UL}y$ (or $^{LL}y$) axis, we can assume that this degree of freedom for the alignment is 0, because the way of fixation prevents the respective position and orientation indicator from rotating around this axis with respect to the body part. So then the full alignment quaternion between first/second body part 3, 5 and the respective position and orientation indicator 2, 4 is given by equation (5).

According to the example provided above, first the rotation axis of a joint is determined from position and orientation indicator readings of a first position and orientation indicator and a second position and orientation indicator and thereafter the alignment of a position and orientation indicator with respect to a body part to which it is attached is determined exploiting both physical constraints to motion due to the physiology of the joint and physical constraints to motion of the position and orientation indicator due to the way of attachment of the position and orientation indicator to the body part.

Further, although the embodiment has been explained with respect to motion of a knee joint and position and orientation indicators attached to the upper and lower legs, the invention is not limited to this. The motion of at least one position and orientation indicator attached to a different body part can be exploited. Further, the joint the motion of which is exploited is not restricted to a knee joint and can also be formed by a different joint. Although attachment of the position and orientation indicators to the body part by means of flexible elastic straps has been described, the way of attachment is not limited to this and other ways of attachment such as by means of a suitable adhesive or the like are also possible.

It should be noted that, according to a modification, more than one degree of freedom of the position and orientation indicator with respect to the body part can be fixed. For example, the position and orientation indicator can be placed in a kind of sock to be worn on a foot such that alignment of the position and orientation indicator around its local z-axis is restricted similar to the example given above. Further, since the sock has a heel, it cannot be worn "backwards" or "upside down" such that it also restricts alignment of the position and orientation indicator around its local x-axis. Such a restriction enables more easily determining the alignment of the position and orientation indicator with respect to the body part. A similar arrangement restricting two degrees of freedom can also be realized with respect to an attachment structure for covering the elbow or the knee (e.g. a specifically shaped textile strap).

Although a specific limitation of the motion range and of the direction of motion which is typical for a knee joint or elbow joint has been described, the invention is not restricted to such specific constraints to motion. Further examples for constraints to motion which can be exploited are shown in FIGS. 7a and 7b. FIG. 7a illustrates that, when a human arm is extended to the front with the palm of the hand upwards, it is not possible to rotate the elbow inward or outward because the elbow does not have this degree of freedom). This physiological constraint can also be exploited for automatic position and orientation indicator alignment. FIG. 7b illustrates that it is not possible to rotate feet backward, a constraint to motion which can also be exploited. It should be noted that all joints comprise physiological motion constraints. These can be exploited for position and orientation indicator alignment.

Although it has been described with respect to the embodiment that the degrees of freedom and the motion range of a joint are exploited for alignment of a position and orientation indicator with respect to a body part, the invention is not restricted to this and other measures can be used to determine whether a motion is "impossible" (and thus only measured due to a misalignment of the position and orientation indicator(s) and the corresponding body part(s)). For example, the following physical constraints to motion can also be exploited:

- It can be exploited that it is not possible that two body parts take the same volumetric position. For instance it is not possible to move an arm 'through' another arm or through the chest. This requires that those other body parts are modeled and equipped with position and orientation indicators.
- It can be exploited that it is not possible that body parts go through other objects (such as a table or the ground surface). This requires that those other objects are also modeled in the virtual world of the computer.
- It can be exploited that the speed with which body parts can move is limited.
- It can be exploited that the acceleration with which body parts can move is limited.

Although it has been described that the motion of a first position and orientation indicator attached to a body part with respect to a second position and orientation indicator attached to a body part is measured, it is also possible to measure the movement of a position and orientation indicator attached to a body part with respect to a world fixed position.

The invention claimed is:

1. A method for automatic alignment of a position and orientation indicator with respect to a body part, the method comprising:

attaching the position and orientation indicator to the body part,
        wherein the body part comprises physiological motion constraints that restrict motion of the body part,
        wherein the body part is unrestrained to be physically free to move within an unrestrained range of motion limited by the physiological motion constraints,
        wherein the attaching attaches the position and orientation indicator such that a motion of the position and orientation indicator has physical motion constraints while allowing unrestrained movement of the body part about at least one axis;
    measuring a movement of the position and orientation indicator that is being moved, when the body part is being moved
    based on the measured movement of the position and orientation indicator, using controller circuitry, determining the alignment of the position and orientation indicator with respect to the body part by exploiting physical constraints to motion so as to obtain an alignment result;
    using the controller circuitry, during the moving the body part unrestrained including the unrestrained movement of the body part about the at least one axis within the unrestrained range of motion, judging that an alignment fault is present upon a motion beyond the unrestrained range of motion of the body part being detected which is not possible in view of the physical constraints; and automatically aligning a local position and orientation indicator coordinate frame of the position and orientation indicator with a local body part coordinate frame of the body part based on the alignment result, wherein the physical constraints include the physiological motion constraints of the body part and the physical motion constraints of the motion of the position and orientation indicator constrained by the attaching.

2. The method according to claim 1, wherein the body part comprises at least one joint, and physiological motion constraints of the at least one joint are exploited as physical constraints to motion.

3. The method according to claim 2, wherein the body part is an arm and the at least one joint is an elbow or wherein the body part is a leg and the at least one joint is a knee.

4. The method according to claim 1, wherein the position and orientation indicator comprises local coordinate system ($US_x$, $US_y$, $US_z$, $LS_x$, $LS_y$, $LS_z$) and is attached to the body part such that the rotation ($R_z$) about the at least one axis ($US_z$, $LS_z$) of the local coordinate system with respect to the body part is prevented.

5. The method of claim 4, wherein the position and orientation indicator is attached to the body part such that rotation about two axes ($US_z$, $US_x$, $LS_z$, $LS_x$) of the local coordinate system with respect to the body part is prevented.

6. The method according to claim 1, wherein the measuring of the movement of the position and orientation indicator includes measuring a movement of a first position and orientation indicator with respect to a second position and orientation indicator, and at least one of the first position and orientation indicator and the second position and orientation indicator is attached to the body part.

7. The method according to claim 6, wherein the first position and orientation indicator is attached to the body part on one side of at least one joint and the second position and orientation indicator is attached to the body part on the opposite side of the at least one joint.

8. The method of claim 1, wherein the body part includes a joint and the physiological motion constraints comprise constraints of the joint on a range of motion of the joint, and wherein the method further comprises acts of:

measuring the unrestrained movement of the joint; and
updating the alignment when the measured unrestrained movement of the joint is greater than a maximum range of motion of the joint limited by the physiological motion constraints of the joint.

9. The method of claim 1, wherein the determining determines the alignment based on knowledge by the controller circuitry that a first motion can be caused by the body part and not by the position and orientation indicator.

10. A device comprising:

a position and orientation indicator adapted for being attached to a body part, wherein the body part unrestrained to be physically free to move within an unrestrained range of motion limited by physiological motion constraints of the body part and physical motion constraints due to attachment of the position and orientation indicator to the body part, wherein the physical motion constraints allow rotation of the body part about at least one axis; and controller circuitry configured to:

measure a movement of the position and orientation indicator that is being moved, when the body part is being moved unrestrained about the at least one axis within the physiological motion constraints;

based on the measured movement of the position and orientation indicator, determine the alignment of the position and orientation indicator with respect to the body part by exploiting physical constraints to motion to obtain an alignment result, the physical constraints including the physiological motion constraints of the body part and physical motion constraints of motion of the position and orientation indicator;

during movement of the body part unrestrained about the at least one axis within the unrestrained range of motion, judge that an alignment fault is present upon a motion beyond the unrestrained range of motion of the body part being detected which is not possible in view of the physical constraints; and automatically align a local position and orientation indicator coordinate frame of the position and orientation indicator with a local body part coordinate frame of the body part based on the alignment result.

11. The device according to claim 10, wherein the device comprises at least a first position and orientation indicator and a second position and orientation indicator, wherein the controller circuitry is configured to measure a movement of the first position and orientation indicator with respect to the second position and orientation indicator.

12. The device according to claim 11, wherein the first and second position and orientation indicators are adapted for attachment to the body part on opposite sides of at least one joint.

13. The device according to claim 10, wherein the device is a physiotherapy monitoring device.

14. The device according to claim 10, wherein the position and orientation indicator is formed using a motion sensor.

15. The device of claim 10, wherein the controller circuitry is configured to determine the alignment based on knowledge that a first motion can be caused by the body part and not by the position and orientation indicator.

* * * * *